(12) United States Patent
Pickardt et al.

(10) Patent No.: US 9,351,514 B2
(45) Date of Patent: May 31, 2016

(54) PROTEIN PREPARATION PRODUCED FROM RAPE SEEDS

(75) Inventors: Claudia Pickardt, Freising (DE); Peter Eisner, Freising (DE); Stephanie Bader, Freising (DE); Klaus Muller, Freising (DE); Hubert Zimmermann, Mettmenstetten (CH); Etienne Bernath, Ruschlikon (CH); Florian Wild, Freising (DE); Michael Frankl, Munich (DE); Sigrid Gruppe, Allershausen (DE); Klaus Schreiber, Freising (DE)

(73) Assignee: FRAUNHOFER-GESELLSCHAFT ZUR FORDERUNG DER ANGEWANDTEN FORSCHUNG E.V., Munich (DE)

( * ) Notice: Subject to any disclaimer, the term of this patent is extended or adjusted under 35 U.S.C. 154(b) by 671 days.

(21) Appl. No.: 13/201,480

(22) PCT Filed: Feb. 26, 2010

(86) PCT No.: PCT/CH2010/000047
§ 371 (c)(1),
(2), (4) Date: Aug. 15, 2011

(87) PCT Pub. No.: WO2010/096943
PCT Pub. Date: Sep. 2, 2010

(65) Prior Publication Data
US 2011/0301074 A1    Dec. 8, 2011

(30) Foreign Application Priority Data

Feb. 27, 2009    (DE) .......................... 10 2009 010 813

(51) Int. Cl.
| | |
|---|---|
| *A23L 1/305* | (2006.01) |
| *A23J 1/14* | (2006.01) |
| *A23K 1/14* | (2006.01) |
| *A23K 1/16* | (2006.01) |
| *A23K 1/18* | (2006.01) |
| *A61K 8/64* | (2006.01) |
| *A61Q 19/00* | (2006.01) |

(52) U.S. Cl.
CPC .............. *A23L 1/3055* (2013.01); *A23J 1/142* (2013.01); *A23K 1/14* (2013.01); *A23K 1/1631* (2013.01); *A23K 1/188* (2013.01); *A61K 8/645* (2013.01); *A61Q 19/00* (2013.01)

(58) Field of Classification Search
None
See application file for complete search history.

(56) References Cited

U.S. PATENT DOCUMENTS

| | | | |
|---|---|---|---|
| 4,158,656 A * | 6/1979 | Jones et al. ................... 530/377 |
| 4,219,469 A | 8/1980 | Kadan et al. | |
| 4,244,973 A * | 1/1981 | van Megen ...................... 426/49 |
| 4,418,013 A * | 11/1983 | Cameron et al. .............. 530/377 |
| 6,335,044 B1 | 1/2002 | Wasche et al. | |
| 6,992,173 B2 | 1/2006 | Milanova et al. | |
| 7,074,449 B1 | 7/2006 | Holley et al. | |
| 7,678,392 B2 | 3/2010 | Green et al. | |
| 7,687,087 B2 | 3/2010 | Barker et al. | |
| 7,790,207 B2 | 9/2010 | Green et al. | |
| 7,794,762 B2 | 9/2010 | Barker et al. | |
| 8,128,974 B2 | 3/2012 | Barker et al. | |
| 2005/0031767 A1 | 2/2005 | Schweizer et al. | |
| 2007/0065567 A1 | 3/2007 | Segall et al. | |
| 2007/0178566 A1 | 8/2007 | Schweizer et al. | |
| 2009/0175999 A1 | 7/2009 | Segall et al. | |
| 2009/0286961 A1 | 11/2009 | Tang | |
| 2010/0048874 A1 | 2/2010 | Green et al. | |
| 2010/0136173 A1 | 6/2010 | Tang | |

FOREIGN PATENT DOCUMENTS

| | | |
|---|---|---|
| CN | 1523961 A | 8/2004 |
| CN | 1674789 A | 9/2005 |
| CN | 1837234 A | 9/2006 |
| DE | 2 421 270 A1 | 12/1974 |
| DE | 199 12 037 A1 | 6/2002 |
| EP | 1 513 415 B1 | 5/2009 |
| GB | 1 428 076 A | 3/1976 |
| UA | 25 695 U | 8/2007 |
| UA | 25695 | 8/2007 |
| WO | 2004/000032 A2 | 12/2003 |
| WO | 04000032 A2 | 12/2003 |
| WO | 2007/033481 A1 | 3/2007 |
| WO | 2007033481 A1 | 3/2007 |
| WO | 2009/137934 A1 | 11/2009 |

(Continued)

OTHER PUBLICATIONS

International Search Report, dated Oct. 29, 2010, from corresponding PCT application.

(Continued)

*Primary Examiner* — Maury Audet
(74) *Attorney, Agent, or Firm* — Young & Thompson

(57) ABSTRACT

The protein preparation produced from rape seeds has a protein content of less than 90% based on the dry mass, has a brightness L*, determined according to CIE-L*a*b* color scale, of at least 70 and also has at least water-binding, oil-binding and emulsifying functionality. The method for producing a protein preparation includes dehulling the rape seeds and a mechanical deoiling process, wherein only part of the oil is separated and/or wherein the process is carried out at a temperature, averaged over the duration of the pressing process, of less than 80° C., and/or an extraction process wherein the amount of non-protein material is reduced in the protein flour and then the grain size is prepared in order to obtain a pourable material having a predetermined particle size distribution.

21 Claims, No Drawings

(56) References Cited

FOREIGN PATENT DOCUMENTS

| WO | 2010/097237 A1 | 9/2010 |
|---|---|---|
| WO | 2010/097238 A2 | 9/2010 |

OTHER PUBLICATIONS

Yumiko Yoshie-Stark et al., "Functional and bioactive properties of rapeseed protein concentrates and sensory analysis of food application with rapeseed protein concentrates", LWT, 2006, pp. 503-512, vol. 39.

H. Kozlowska et al., "The influence of selected technological processes on the improvement of rapeseed meal and fluor feed quality. Part 1. The influence of hydrothermal treatment and ethanol extraction on chemical composition of rapeseed products", Die Nahrung, 1991, pp. 485-489, vol. 35, No. 5.

Felix H. Schneider et al., "Trennpressen geschalter Rapssaat—Zielsetzung und verfahrenstechnische Probleme", Fett/Lipid, 1997, pp. 91-98, vol. 99, No. 3; English-language Abstract.

C.V. Morr et al., "A Collaborative Study to Develop a Standardized Food Protein Solubility Procedure", Journal of Food Science, 1985, pp. 1715-1718, vol. 50.

American Association of Cereal Chemists, "Hydration Capacity of Pregelatinized Cereal Products", AACC Method 56-20, Physicochemical Tests.

I. Ludwig et al., "Eine Mikromethode zur Bestimmung der Fettbindekapazitat von Proteinen", Die Nahrung, 1989, pp. 99-101, vol. 33, No. 1.

A. Wasche et al., "New processing of lupin protein isolates and functional properties", Nahrung/Food, 2001, pp. 393-395, vol. 45, No. 6.

Ch. Gertz et al., "Determination of fat content by the Caviezel method (rapid method)", Eur. J. Lipid Sci. Technol., 2000, pp. 154-158.

Isabel M.N. Sousa et al., "Differential scanning calorimetry of lupin and soy proteins", Z Lebensm Unters Forsch, 1995, pp. 566-569, vol. 201.

Ping et al., "Study on Extraction Isolation of Rapeseed Meal Protein", Resource Development & Market, 2007, vol. 23, No. 6, pp.

Chinese Office Action, from corresponding CN application.

\* cited by examiner

PROTEIN PREPARATION PRODUCED FROM RAPE SEEDS

The present invention relates to a protein preparation produced from rape seeds and to a method for producing such a protein preparation.

Protein preparations are frequently used in foodstuffs as nutritionally or techno-functionally active ingredients. There are protein preparations with a particularly high protein value used as high-quality food additives (baby food, special food, sports food). They are principally also of interest for the formulation of feedstuff in which a high protein availability has to be ensured. Other protein preparations have a good techno-functionality and, e.g., are suitable to stabilize foams or emulsions or to form gels. These protein preparations are primarily suited as food ingredients and are also used for special feedstuffs or technical purposes.

Principally, protein preparations of animal or plant origin can be distinguished.

Examples of protein preparations of animal origin are such made of hen's eggs, milk, whey or casein and gelatin preparations from slaughterhouse waste. The disadvantage is that such protein preparations have a characteristic intrinsic taste and intrinsic odor and are therefore limited to certain applications. They are often expensive to produce and problematic with respect to allergies and are rejected by certain consumers for ethical reasons.

As alternative protein sources of plant origin, primarily preparations from soy proteins and wheat gluten are used. However, the application range of the same in case of foodstuffs and feedstuffs is limited, among other things due to substances which affect the smell or taste and/or are allergenic and/or due to dark color.

Likewise, plant protein preparations are known which are produced from rape seeds in the form of rape seed concentrates or rape protein isolates.

In comparison to rape protein concentrates, rape protein isolates have a very high protein content which is at least 90% based on the dry mass. However, rape protein concentrates usually contain the entire amino acid spectrum of the rape seed used during the production. They have a balanced amino acid spectrum and are suitable, among other things, for protein enrichment in foodstuffs and feedstuffs.

The production of rape protein concentrates requires special measures if components which are undesirable for special applications such as glucosinolates, phenolic acids and phytic acids have to be removed. For this purpose, an extraction with diluted aqueous-alcoholic solutions has been proposed. For example, in the literature, rape protein concentrates are described which were obtained by extraction with 45% isopropanol (see Yumiko Yoshie-Stark et al., "Functional and bioactive properties of rapeseed protein concentrates and sensory analysis of food application with rapeseed protein concentrates", LWT 39 (2006) 503-512) or with 80% alcohol in connection with high temperatures of 60° C. (see Kozlowska et al., "The influence of selected technological processes on the improvement of rapeseed meal and fluor feed quality. Part 1.", Die Nahrung 35 (1991) 5, 485-489).

With these two methods, rape protein concentrates are produced in that prior to the extraction, deoiling takes place exclusively by means of solvents. After the extraction of the non-protein substances, no further treatments are provided. Said methods, among other things, have the disadvantage that the functional properties of the rape protein concentrates are difficult to be preset. Also, in the above-mentioned article of Yumiko Yoshie-Stark et al. it is reported that sausages for which the produced rape protein concentrate was used showed a drastic color deterioration.

Along with the extraction, preparing the rape seeds can already be a problem if this is not carried out gentle enough. In the magazine article of Felix H. Schneider and Michael Rass, "Trennpressen geschälter Rapssaat—Zielsetzung and verfahrenstechnische Probleme", Fett/Lipid 99 (1997) No. 3, 91-98, a method is described in which dehulled rap seeds are deoiled by means of a screw press and subsequently by means of hexane at a temperature of 60 degrees Celsius. No special measures are provided for a gentle deoiling so that the proteins can be excessively denatured.

In summary, the known rape protein concentrates which have a low purification degree, are limited with respect to their functionality and/or contain a certain proportion of undesirable components which can negatively influence the nutritional value, the color, the smell and/or taste of the foodstuffs or groceries containing the same. Thus, the rape protein concentrates have a limited application range and can only be used in low concentrations.

Rape protein isolates as described e.g. in EP 1 513 415 B1, have a high purification degree and are therefore complicated and expensive to produce. They contain only a proportion of individual components of the original protein matrix of the rape seed and thus have a specific nutritional and techno-functional profile with few particularly outstanding properties. Their application spectrum is very specific and limited to few applications.

It is an object of the present invention to provide protein preparations which are relatively inexpensive to produce and can be used in many applications.

This object is solved with a protein preparation which is defined in claim 1 or is produced with the method according to the independent method claim. The further claims define preferred embodiments of the protein preparation and the method according to the invention as well as a product produced with a protein preparation according to the invention and a method for recovering energy from the rape hulls produced during dehulling the rape seeds.

The protein preparation according to the invention has a lower protein content than protein isolates and is suitable for a more cost-effective production because a high purification as it is required in case of protein isolates can be avoided.

Surprisingly, despite the higher proportion of non-protein substances, the protein preparation according to the invention has properties which are similar to the ones of the known rape protein isolates or are even more versatile than the latter. Due to the bright color and the balanced techno-functional spectrum in the form of water-binding, oil-binding and emulsifying function, the protein preparation can be used in many applications, amongst others in foodstuffs and feedstuffs, for binding water and/or oil, or for forming an emulsion. Said protein preparation is suitable to replace other preparations which were previously used for these functions and which are of animal or plant origin such as hen's egg, milk, soy, rape in the form of rape isolates, etc.

Further, surprisingly, if present in the form of rape protein flour, which is particularly inexpensive to produce, the protein preparation has properties with respect to color and functionalities which allow to use the rape protein flour in a plurality of foodstuff and feedstuff applications.

The field of use of the protein preparation according to the invention can be extended if the protein preparation is free of the plant-inherent or seed-inherent flavors of the rape, in particular if it is substantially odorless and/or substantially tasteless. This prevents, among other things, that when incorporating the protein preparation into the foodstuffs and feedstuffs, an undesired change of taste and flavor takes place.

Also, by obtaining a foam-forming functionality, the field of use can be extended so that the protein preparation can be used, e.g. as substitute for hen's egg white or other foam-forming additives so as to produce foam-like foodstuffs.

Preferably, the protein preparation has a low fat content, whereby a good storage stability of the protein preparation is ensured.

More preferably, the protein preparation has a low content of phytic acid, glucosinolates and/or phenolic acid. Thereby, the risk is reduced that during digestion, the processing of nutrients is affected.

The method according to the invention allows a gentle production of the preparation so that an undesired denaturation of the proteins is prevented and allows to obtain protein preparations of premium and high sensory quality and a broad application spectrum.

If a partial deoiling is provided during the mechanical deoiling, the treatment is particularly gentle and the subsequent method steps can be simplified, e.g. by eliminating a mechanical comminution prior to the extraction.

If during the mechanical deoiling, an excessive temperature is avoided, it is in particular possible to avoid undesirable protein alterations or reactions of the non-protein substances with the proteins.

During the production of a protein concentrate, a gentle treatment can also be achieved by providing an extraction in which the non-protein substances in the protein flour are depleted. By subsequently preparing the grain size, the functional properties of the protein concentrate can be preset in an improved manner.

Preferably, the method is carried out such that the extraction by means of the extraction solvent is carried out in a plurality of extraction steps, wherein during at least one transition from the one to the next extraction step, the alcohol content in the extraction solvent is increased. This allows to perform the subsequent drying process in a particularly gentle manner because the content of the residual water to be removed, which evaporates slower and at a higher temperature than the alcohol, is reduced.

An additional benefit in the form of energy recovery can be achieved by burning up the hulls produced during dehulling the rape seeds.

Further advantages arise from the features according to the dependent claims and the following description in which the invention is illustrated by means of exemplary embodiments.

Unless otherwise stated, the contents expressed below as percentages are based in case of liquids on percent by volume (v/v) at a temperature of 25 degrees Celsius and in case of solids on percent by mass (w/w).

A) PRODUCTION METHOD

For example, the protein preparation according to the invention can be produced from rape according to the following method. For this, any rape can be used, even a specifically farmed raped (e.g. of the type "00-rape", in English "Canola") and/or a genetically modified one. The method comprises the following method steps V1-V8:

V1 Pretreatment:
  The rape seed is dried after harvesting at a product temperature of less than 95° C., preferred less than 40° C. for a heating time which lies typically in the range of 10-20 min. A higher product temperature is conceivable if the contact time is short, i.e. less than 20 min and preferably less than 5 min. By the drying process is achieved that the rape seed has a water content of less than 9% w/w, preferred less than 8% w/w and particularly preferred less than 7% w/w. Furthermore, the drying process is specifically carried out such that, on the one hand, enzymes which subsequently would disturb the method or the quality of the end product are inactivated and, on the other, a denaturation of the storage protein, which represents the main portion of the proteins, takes place to a limited extent. Thus, by the inactivation of the enzymes such as myrosinase, lipoxygenase and polyphenoloxidase it can be prevented, among other things, that subsequently, a release of odor and taste active mustard oils, a fat cleavage and/or color change takes place.

V2 Dehulling:
  The rape seeds which consist of kernel and hulls are dehulled by breaking-up in a mill and separating in an air stream into a kernel-rich and a hull-rich fraction. The dehulling process is configured such that the kernel fraction used in the subsequent method step V3 has a hull content of less than 15% w/w, preferred less than 5% w/w and particularly preferred less than 1% w/w. If necessary, the dehulling process comprises in addition a sieving of the rape seed or the fractions and/or a further classifying of the fractions so as to obtain a sufficiently purified kernel fraction.

V3 Mechanical Treatment:
  The kernel fraction is mechanically partially deoiled, e.g. by means of a press, to a residual oil content of 10-30% w/w, preferably 15-25% w/w. The temperature Tm of the kernel fraction averaged over the duration of the pressing process lies below 80° C., preferred below 60° C. This does not exclude that the temperature of the kernel fraction at a certain time and/or the local temperature of individual kernels is higher than Tm. If necessary, cooling is provided to dissipate the heat which is generated during the mechanical deoiling, e.g. due to the pressure during pressing. It is conceivable to provide, alternatively or additionally to the mechanical deoiling, a mechanical treatment in the form of flaking.

V4 Solvent Deoiling:
  The pressing residue ("rapeseed cake") obtained in the method step V3 is deoiled with n-hexane, iso-hexane or another suitable solvent at temperatures below 90° C., preferably below 60° C. and the solvent is removed, e.g. by means of flash desolventizing. The deoiled residue has a residual content of oil of less than 6% based on the dry mass (determined according to the Caviezel method) and is hereinafter also called rape protein flour.

V5 Aqueous-alcoholic Extraction:
  The deoiled residue is treated with aqueous alcohol with an alcohol content between 60 and 95% v/v, preferably between 70 and 80% v/v. During the aqueous-alcoholic extraction, the accompanying substances of protein such as sugar, secondary plant substances, etc. are depleted while the proteins for the most part do not go into solution. (Accordingly, this method differs from the production of rape protein isolates in which the proteins are extracted from the fiber matrix and are subsequently recovered from the solution, e.g. by precipitation and/or a membrane process.) After the extraction, the alcohol is removed, preferably by using a vacuum at temperatures of maximum 60° C. and/or by using alcohol vapor or water vapor for expelling the alcohol at a temperature below 60° C.

V6 Drying:
  The protein concentrate obtained in method step V5 is dried. The temperature is selected here, among other things, depending on the residual water content and lies typically in the range of 50 to 90° C., preferred below 70° C. and particularly preferred below 60 C.°. Optionally, drying is carried out using a vacuum.

V7 Optional Mechanical Separation:
If necessary, the protein concentrate obtained in the method step V6 is classified and/or sieved so as to modify the functional properties and/or the color and to separate any present hull particles.

V8 Further Preparation of the Grain Size:
The obtained protein concentrate is brought in such a pourable form that it has a certain grain size. This is carried out e.g. by sieving, classifying, fine milling or granulating the powder obtained in method step V6 or V7. The finally obtained rape protein concentrate is hereinafter also referred to as RPC.

It is possible to omit the method step V5 and to process the deoiled residue obtained in method step V4 according to the method steps V6, V7 and/or V8. Thereby, a protein preparation in the form of rape protein flour (RPF) is provided.

It was found that due to preparing the grain size according to the aforementioned method step V7 or V8, a further improvement of the properties of the protein preparation and/or a specific setting of the functional properties can be achieved. It was in particular found that the water-binding properties and oil-binding properties as well as the emulsifying properties change in different ways by fine milling the rape protein flour or rape protein concentrate. Thus, depending on the purpose of use, a higher water-binding and oil-binding capability can be established by a systematic milling and further properties such as emulsifying capacity can be changed.

Further details of the method can be found in the unpublished German Patent Application 10 2009 010 813.0, filed on Feb. 27, 2009, the content of which is hereby included in full in the description of the present application.

B) CHARACTERIZATION OF THE PRODUCED PROTEIN PREPARATION

By means of the above-described production method, a protein preparation can be obtained which is characterized, e.g. with respect to protein isolates which are obtained by aqueous fractionation and complex isolation methods, by a balanced nutritional profile and a techno-functional spectrum. The protein preparation is suitable, among other things, as foodstuff or feedstuff additive even without further processing, e.g. so as to obtain the high protein content of a protein isolate. Surprisingly, although it is not a protein isolate, the protein preparation shows the techno-functional properties of protein isolates. It has neutral, typically yellow color and is largely free of sensorially disturbing and antinutritive accompanying substances. In particular, in the form of rape protein concentrate, it has almost no intrinsic odor and intrinsic taste.

It is particularly surprising that already the deoiled rape protein flour (RPF) has an extremely appealing color and a well-developed functionality and is suitable for many foodstuff and feedstuff applications.

Below, the following determination methods are used for the quantitative characterization of the produced protein preparations:

Protein Content:
The protein content is defined as the content which is calculated from the determination of the nitrogen and the multiplication of the same by the factor 6.25. The protein content can be expressed e.g. as a percentage based on the dry mass (DM).

Color:
Perceptible color is defined by means of CIE-L*a*b* color scale (cf. DIN 6417). Here, the L*-axis indicates the brightness, wherein black has the value 0 and white has the value 100, the a*-axis describes the green or red portion and the b*-axis describes the blue or yellow portion.

Protein Solubility:
The protein solubility is determined by means of the determination method according to Morr et al. 1985 (hereinafter called PN determination method), see magazine article: Morr C. V., German, B., Kinsella, J. E., Regenstein, J. M., Van Buren, J. P., Kilara, A., Lewis, B. A., Mangino, M. E, "A Collaborative Study to Develop a Standardized Food Solubility Procedure. Journal of Food Science", volume 50 (1985) pages 1715-1718).

With the PN determination method, the protein preparation is suspended at room temperature in a mass-volume proportion of 1:25 to 1:50 (w/v) (i.e. 1-2 g of the protein preparation in 50 ml solution) in a 0.1 M NaCl solution and, by using 0.1 M HCl or NaOH solution, is maintained at a pH value of pH 7 for approximately 60 min and is stirred at approximately 200 rpm, and the insoluble sediment is subsequently removed by centrifuging for 15 min at 20,000 times gravity (20,000 g). The protein solubility can be expressed e.g. as a percentage, wherein a protein solubility of x % means that x % of the protein present in the preparation are found again in the clarified supernatant when the PN determination method is used.

Water Binding:
Water binding ability is defined by means of the determination method (hereinafter called AACC determination method) as specified in: American Association of Cereal Chemists, "Approved methods of the AACC". 10th ed., AACC. St. Paul, Minn., 2000b; Method 56-20. "Hydration capacity of pregelatinized cereal products". Water binding ability can be expressed e.g. in ml/g DM, i.e. milliliter bound water per gram of dry mass and is determined according to the AACC determination method via the weight of the sediment saturated with water less the weight of the dry preparation after mixing approx. 2 g of protein preparation with approx. 40 ml of water for 10 min and centrifugation at 1,000 g for 15 min at 20° C.

Oil Binding:
Oil binding ability is defined by means of the determination method (hereinafter called OB determination method) as specified in: Ludwig I., Ludwig, E., Pingel B., "Eine Mikromethode zur Bestimmung der Fettbindkapazität". Nahrung/Food, 1989, 33(1), 99. The oil binding ability can be expressed e.g. in ml/g, i.e. milliliter bound oil per gram of preparation and is measured according to the OB determination method as volume of the oil-binding sediment after mixing 1.5 g of protein preparation with 15 ml of corn oil for 1 min and centrifugation at 700 g for 15 min at 20° C.

Emulsifying Capacity:
Emulsifying capacity is determined by means of the determination method (hereinafter called EC determination method), wherein corn oil is added to a 1% suspension of the protein preparation of 100 ml, pH 7, until phase inversion of the oil-in-water emulsion. Emulsifying capacity is defined as the maximum oil absorption ability of this suspension, determined via the spontaneous decrease of the conductivity during the phase inversion (cf. magazine article of Wasche, A., Müller, K., Knauf, U., "New processing of lupin protein isolates and functional properties". Nahrung/Food, 2001, 45, 393-395) and can be expressed e.g. in ml/g, i.e. milliliter of emulsified oil per gram of preparation.

Foam Activity:
  Foam activity is expressed as a percentage, measured as volume increase of a 5% solution, pH 7, when beating for 8 min at setting 3 (591 rpm) in a Hobart 50N standard kitchen machine (steel container with a capacity of 5 liters) with a beater (wire beater).

Foam Density:
  Foam density is expressed in g/l, i.e. mass of the foam per volume unit, and is measured after beating a 5% solution, pH 7, for 8 min at setting 3 (591 rpm) in a Hobart 50N standard kitchen machine (steel container with a capacity of 5 liter) with a beater (wire beater).

Foam Stability:
  Foam stability is expressed as a percentage, measured as volume decrease of 100 ml of foam within one hour after beating a 5% solution, pH 7, for 8 min at setting 3 (591 rpm) in a Hobart 50N standard kitchen machine (steel container with a capacity of 5 liter) with a beater (wire beater).

Fat Content:
  Fat content is determined after sample disintegration and saponification of the fatty acids e.g. according to the Caviezel method (described in DGF. "Method of Caviezel", DGF K-I 2c (00). In: DGF-Einheitsmethoden, Deutsche Gesellschaft für Fettwissenschaften e.V., Münster, WVG, Stuttgart, 2nd edition, 2004.).

Denaturation:
  Denaturation is expressed as a percentage and is measured e.g. by comparing the denaturation properties of the main protein fraction of the rape kernels before and after heating by means of "Differential Scanning calorimetry", as described in the magazine article: Sousa, I. M. N., Mitchell, J. R., Ledward, D. A., Hill, S. E., Beirfio da Costa, M. L., "Differential Scanning calorimetry of lupin and soy proteins". Zeitschrift für Lebensmitteluntersuchung und-Forschung, volume 201 (1995), 566-569.

For comparison purposes, the following commercially produced products were used:
  pea protein isolate Pisane® (produced by Cosucra),
  soy protein isolate SUPRO® EX33 (produced by DuPont),
  sodium caseinate (spray-dried), FN5S from Rovita.

With the production method according to the invention, protein preparations can be produced which typically have the following properties:

Appearance:
  In pourable form e.g. as flakes, granulate, powder or in the form of other particles.
  The color is white to cream, light gray or light yellow to deep yellow, possibly with a portion of dark-colored particles of maximum 5% w/w, preferably less than 2% w/w. The brightness $L^*$ according to CIE-$L^*a^*b^*$ color scale yields a value of at least 70, $L^*>=70$. The following are typical values for $L^*$, $a^*$ and $b^*$:
    $L^*>=80$, $-5<a^*<+5$, $-5<b^*<+30$; preferably
    $L^*>=85$, $-1<a^*<+5$, $0<b^*<+25$; particularly preferred
    $L^*>=90$, $-1<a^*<+3$, $0<b^*<+20$.

Composition:
  The protein content is less than 90% in the dry mass (DM) and/or less than 80% based on DM. Typically, the protein content lies between 40 and 70% based on DM and/or between 45 and 65% based on DM.
  Crude fiber content between 3 and 20% based on DM, preferred between 5 and 10% based on DM.
  The content of total dietary fibers is typically 20-40%, the content of insoluble dietary fibers/ADF ("Acid detergent fiber") is typically 8-20%.
  Fat content, determined e.g. by gravimetric analysis after Soxhlet extraction, typically less than 6% based on DM, preferred less than 1%.
  Sugar content less than 10% based on DM, preferred less than 5%, particularly preferred less than 2%.
  Content of harmful substances, in particular anti-nutritive substances:
    Phytic acid content less than 10% based on DM, preferred less than 5%, particularly preferred less than 3%.
    Glucosinolate content (content of mustard oil compounds) less than 4000 mg per kg of protein preparation, preferred less than 2500 mg/kg, particularly preferred less than 1500 mg/kg. In particular, the progoitrin content is less than 1000 mg/kg, preferred less than 500 mg/kg, particularly preferred less than 200 mg/kg.
    Phenolic acid content (determined as sinapinic acid) less than 5% based on DM, preferred less than 2%, particularly preferred less than 0.5%.
  Lignin content less than 6% based on DM, preferred less than 4%, particularly preferred less than 3%.
  In general, the protein content as well as the lignin content of the rape protein flour (RPF) is lower than the one of the rape protein concentrate (RPC) produced therefrom, whereas the content of fat, sugar and phenolic acid in RPF is higher than the one in RPC.
  The amino acid composition is balanced with a high protein value compared to commercially available plant protein concentrates, wherein the lysine content with regard to the total protein is at least 4%, preferred at least 5% and the content of sulfur-containing amino acids (sum of methionine and cysteine) with regard to the total protein is at least 3%, preferred at least 4%. The original amino acid composition of rape seed is substantially maintained in case of the protein preparation.
  The denaturation is typically in the range of 5% to 40% and/or in the range of 10% to 20%.

Techno-functional Properties:
  Protein Solubility:
    The protein solubility, determined according to the PN determination method, is greater than 40%, preferred greater than 60%.
    Typically, the protein solubility in case of the RPF is in the range of 60-70% and in case of the RPC in the range of 45-55%.
  Water Binding:
    The water binding ability, determined according to the AACC determination method, is at least 1 ml/g DM, preferred at least 2 ml/g DM and particularly preferred at least 3 ml/g DM. Comparison measurements show that the water binding ability of the preparation is typically at least 30% of the water binding ability of Pisane®, determined according to the AACC determination method.
  Oil Binding:
    The oil binding ability, determined according to the OB determination method, is at least 1 ml/g, preferred at least 2 ml/g and particularly at least 4 ml/g. Comparison measurements show that the oil binding ability is at least 100% of the oil binding ability of Pisane® or Supro® EX33, determined according to the OB determination method.

Emulsifying Capacity:

The emulsifying capacity, determined according to the EC determination method, is at least 400 ml/g, preferred at least 500 ml/g, particularly preferred at least 600 ml/g. Comparison measurements show that the emulsifying capacity is at least 40% of the emulsifying capacity of sodium caseinate FN5S, determined according to the EC determination method. The emulsifying capacity is typically higher in case of the RPF than in case of the RPC produced therefrom.

Foam Forming Properties:

Foam Activity:

The foam activity is at least 500%, preferably at least 1000%. Comparison measurements with fresh hen's egg whites beaten for 3 min on setting 3 in a Hobart 50N standard kitchen machine with a beater show that the foam activity of the protein preparation corresponds to at least 30% or even at least 60% of the foam activity of hen's egg white.

Foam Density:

The foam density lies in the range of 80 and 110 g/l. Comparison measurements with whipped hen's egg whites beaten for 3 min on setting 3 in a Hobart 50N standard kitchen machine with a beater show that the foam density lies in the range of 80 and 110% of the foam density of whipped egg white.

Foam Stability:

The foam stability is at least 80%, preferably at least 90%. It corresponds typically to at least 90% of the foam stability of whipped hen's egg white, measured as volume decrease of 100 ml whipped egg white within one hour after beating for 3 min on setting 3 in a Hobart 50N standard kitchen machine with a beater.

Sensory Properties:

In addition to the bright color, the protein preparation, in particular in the form of the RPC, is substantially odorless and tasteless. In particular, the plant or seed flavors of the rape are substantially missing. Thus, substantially, no mustard-like, horseradish-like or pungent odor and taste as well as substantially no bitter taste can be sensed.

Sensory tests in which skilled examiners compare a particular taste or flavor impression of the protein preparation and a suitable reference substance and evaluate it on a scale of 1 to 10 (1=not sensible, 10=strongly sensible), wherein the reference substance is selected such that its taste or flavor impression to be tested is evaluated with at least 8, show that a value of 3 or less (typically a value of 1) is assigned to the protein preparation.

Examples for taste or flavor impressions to be tested are:

horseradish-like/pungent odor and taste compared to customary commercially available quality horseradish, e.g. "Meerrettich" from Hengstenberg, mustard-like odor and taste compared to a commercially available quality mustard, e.g. "Löwensenf medium", bitter taste compared to a 0.1% aqueous caffeine solution, astringency (rough, numb mouth feel) compared to a tart red wine or bitter chocolate.

Color, intrinsic taste and intrinsic odor of the protein preparation in the form of the RPC are such that when incorporating it into foodstuffs and feedstuffs, substantially, no significant change determined with statistical methods and to be evaluated as being negative of the characteristic appearance, odor or taste of the finished preparation occurs.

Sensory tests show that the taste and flavor change in a food product caused by the use of the protein preparation is limited with respect to a food product without the protein preparation to such an extent that a skilled examiner can sense a deviation of one of the above-mentioned taste or flavor characteristics (horseradish, mustard, etc.), on a scale of 1-10, of maximum 3 levels or even maximum 1 level (deviation almost not sensible anymore).

C) EXAMPLES

In the following, production method and protein preparation according to the invention are illustrated by means of further examples.

C.1) Example 1

Rape Protein Flour and Rape Protein Concentrate from 90% Dehulled Rape Seeds

Production:
1. Dehulling the rape seeds by breaking-up in an impact mill and separating into a kernel-rich and a hull-rich fraction in the air stream.
2. Sieving the coarse fractions with a sieve of mesh size 1.25 mm so as to remove dehulled kernels and to obtain a purified kernel fraction after passage through the sieve. (In this example, the kernel fraction contains a hull content of approx. 10% w/w).
3. Flaking the purified kernel fraction by means of smooth-rolling so as to obtain rape flakes.
4. Deoiling the rape kernel flakes in the Soxhlet at temperatures of maximum 80° C., primarily below 60° C.
5. Removing the solvent in the air stream at room temperature. The raffinate obtained in this manner results in the rape protein flour mentioned below.
6. Three-fold extraction of the rape protein flour with the 10-fold volume e.g. of a 80% (v/v) isopropanol solution at room temperature in each case for 1 h while stirring and separating the extract via a filter cloth.
7. After the third extraction, the solvent residues are removed by air drying.
8. Milling the raffinate obtained in the above method step 7 in a pin mill with a sieve insert of 1 mm.
9. Secondary drying of the raffinate in a vacuum at maximum 50° C.
10. Sieving the raffinate with a sieve of mesh size 315 micrometer so as to obtain a rape concentrate in the form of a fine powder.

Properties:

The rape protein concentrate obtained in this manner has a protein content of more than 55% in DM. The composition is listed in the table 1 below; some functional properties are listed in the tables 2 and 3 below. These three tables also include the values for the protein preparation in the form of the rape protein flour obtained in the aforementioned method step 5.

By varying the type of alcohol (methanol, ethanol, isopropanol) and the alcohol content (e.g. 70, 80, 90% v/v) in the above-mentioned method step 6, similar protein preparations were produced according to the same method. The color of these different rape protein concentrates was determined according to CIE-L*a*b* resulting in the following mean values and standard deviations:

|  | L* | a* | b* |
|---|---|---|---|
| Mean value of all protein concentrates | 73.5 | 2.6 | 22.0 |
| Standard deviation | 4.7 | 1.3 | 2.9 |

C.2) Example 2

Rape Protein Flour and Rape Protein Concentrate from 100% Dehulled Rape Seeds

Production:
1. Dehulling the rape seeds by breaking-up in an impact mill and separating into a kernel-rich coarse fraction and a hull-rich fine fraction in the air stream.
2. Sieving the coarse fractions with a sieve of mesh size 1.25 mm so as to remove dehulled kernels and to obtain a pre-purified kernel fraction after passage through the sieve.
3. Sorting out of hull particles and unhulled kernels from the pre-purified kernel fraction by color sorting so as to obtain a pure kernel fraction. Accordingly, the kernel fraction is almost free of hulls.
4. Flaking the kernel fraction in the roller mill with two counter-rotating smooth rolls which have a gap of 0.5 mm therebetween.
5. Deoiling the rape flakes with n-hexane in the Soxhlet at temperatures of maximum 80° C., primarily below 60° C.
6. Removing the solvent in the air stream at room temperature. The raffinate obtained in this manner results in the rape protein flour mentioned below.
7. Three-fold extraction of the rape protein flour with the 10-fold volume e.g. of a 70% (v/v) ethanol solution at room temperature in each case for 1 h while stirring and separating the extract via a filter cloth.
8. Two-fold extraction of the raffinate obtained in the method step 7 with 100% ethanol so as to increase the alcohol concentration in the raffinate to at least 90%.
9. Evaporating the alcohol and drying the raffinate obtained in the method step 8 in the rotary evaporator in a vacuum at maximum 50° C. so as to obtain a rape protein concentrate.
10. Milling the rape protein concentrate in a pin mill with sieve insert 0.5 mm so as to obtain the rape protein concentrate in the form of fine powder.

Properties:

The rape protein concentrate obtained in such a manner is a fine, bright powder with a protein content of more than 55% in DM. The composition is listed in table 1; some functional properties are listed in table 2. These two tables also include the values for the rape protein flour obtained in the above-mentioned method step 6.

The rape protein concentrate obtained in such a manner is free of rape-inherent or mustard- and horseradish-like flavor components.

The color of the hull-free rape protein flour obtained in method step 6 and the rape protein concentrate obtained in method step 10 is particularly appealing, i.e. neutral and has the following values according to CIE-L*a*b*:

|  | L* | a* | b* |
|---|---|---|---|
| Rape protein flour | 87.8 | +0.3 | +25.7 |
| Rape protein concentrate | 90.3 | −0.2 | +16.3 |

C.3) Example 3

Rape Protein Flour and Rape Protein Concentrate from Dehulled Rape Seeds

Production:
1. Dehulling the rape seeds by breaking-up in an impact mill and separating into a kernel-rich coarse fraction and a hull-rich fine fraction in the air stream in a zigzag classifier (classifier with particularly good selectivity, wherein the channel in which the air stream rises is divided by walls arranged in zigzags into a plurality of small tubes).
2. Sieving the coarse fraction with a tumbler sieve of mesh size 1.5 mm so as to remove unhulled kernels and to obtain a purified kernel fraction after passage through the sieve.
3. Flaking the kernel fraction into "rape kernel flakes" in the roller mill with two counter-rotating smooth rolls which have a gap of 0.3 mm therebetween at temperatures below 30° C.
4. Deoiling the rape kernel flakes with iso-hexane in a percolator at temperatures of maximum 60° C.
5. Expelling the hexane with superheated hexane vapor in a vacuum (<500 mbar).
6. Expelling further hexane with superheated water vapor in a vacuum (<500 mbar).
7. Removing solvent residues by heating to 60° C. in a vacuum (<500 mbar). The raffinate obtained in such a manner is hereinafter referred to as protein flour.
8. Three-fold extraction of the protein flour with the 5-8-fold mass of a 65% (w/w) ethanol solution at room temperature by circulating the solvent until constancy of the density and separating the extract via a sieve bottom.
9. Two-fold extraction of the raffinate with 94% w/w of ethanol so as to increase the alcohol concentration in the raffinate to at least 90% w/w.
10. Evaporating the alcohol and drying the raffinate obtained in such a manner by heating to 50-60° C. in a vacuum (<300 mbar) so as to obtain a protein concentrate.
11. Milling the protein concentrate in a pin mill with sieve insert 0.5 mm so as to obtain the protein concentrate in the form of a fine powder.

Properties:

The rape protein concentrate obtained in such a manner is a fine bright powder with a protein content of >60% in DM. The composition is listed in table 1 of section D; some functional properties are listed in the tables 2 and 3.

The protein concentrate obtained in such a manner is low in rape-inherent or mustard- and horseradish-like flavor components.

The color of the rape protein flour (RPF) produced in such a manner which is low in hulls and the color of the rape protein concentrate is particularly appealing or neutral and is represented according to CIE-L*a*b* with the following values:

|  | L* | a* | b* |
|---|---|---|---|
| Rape protein flour | 84.8 | −1.7 | +26.7 |
| Rape protein concentrate | 86.2 | −0.1 | +17.4 |

C.4) Example 4

Rape Protein Flour and Rape Protein Concentrate with Specific Properties

In this example, among other things, the modification of the functional properties of the rape protein preparation was investigated during a final preparation of the grain size.

Production:
1. Dehulling the rape seeds by breaking-up in an impact mill and separating into a kernel-rich coarse fraction and a hull-rich fine fraction in the air stream in a zigzag classifier.
2. Sieving the coarse fraction with a tumbler sieve of mesh size 1.5 mm so as to remove unhulled kernels and to obtain a purified kernel fraction after passage through the sieve.
3. Flaking the kernel fraction in the roller mill with two counter-rotating smooth rolls which have a gap of 0.3 mm therebetween at temperatures below 30° C.
4. Deoiling the rape kernel flakes with iso-hexane in a percolator at temperatures of maximum 60° C.
5. Expelling the hexane with superheated hexane vapor in a vacuum (<500 mbar).
6. Expelling further hexane with superheated water vapor in a vacuum (<500 mbar).
7. Removing solvent residues by heating to 60° C. in a vacuum (<500 mbar). The raffinate obtained in such a manner is hereinafter referred to as protein flour.
8. Classifying, sieving and/or milling the protein flour in a pin or impact mill so as to obtain fractions with different hull content and/or different particle size distribution and to modify the functional properties in this manner. The setting of the mills is specified in table 4 in section D.
9. Three-fold extraction of the protein flour with the 5-8-fold mass of a 65% (w/w) ethanol solution at room temperature by circulating the solvent until constancy of the density and separating the extract via a sieve bottom.
10. Two-fold extraction of the raffinate with 94% w/w of ethanol so as to increase the alcohol concentration in the raffinate to at least 90% w/w
11. Evaporating the alcohol and drying the raffinate obtained in such a manner by heating to 50-60° C. in a vacuum (<300 mbar) so as to obtain a protein concentrate.
12. Classifying, sieving and/or milling the protein concentrate in a pin or impact mill (setting see table 4) so as to obtain fractions with different hull content and/or different particle size distribution and to modify the functional properties in this manner.

By preparing the grain size as carried out above in step 8 or step 12, the functional properties of the protein preparation could be changed. For reducing the grain size, besides a pure milling process, a classification or a sieving process, if necessary in connection with a milling process was used. As shown in table 4, with decreasing grain size, water binding tends to increase as well as the emulsifying capacity in case of the rape protein concentrate, whereas oil binding decreased slightly or remained nearly unchanged. As further shown in table 4, preparations with a more homogenous grain size distribution have a higher water binding ability. The combination of fractioning and comminuting was found to be particularly advantageous for increasing water binding. In summary, it is possible to modify the functional profile by a target-oriented preparation of the grain size distribution.

In the examples 1 to 4, flaking was selected as mechanical pretreatment by means of which the kernels were brought into an advantageous form for the subsequent treatment. After this, the kernel fraction was deoiled solely by using a solvent. A prior mechanical deoiling was not carried out. However, it is advantageous to provide the latter if protein preparations are to be produced in a particularly cost-effective manner and/or in larger volumes. Further advantages of mechanical deoiling arise from the example 5 described below.

C.5) Example 5

Rape Protein Flour and Rape Protein Concentrate from Dehulled Rape Seeds

Production:
1. Dehulling the rape seeds by breaking-up in an impact mill and separating into a kernel-rich coarse fraction with a hull content of less than 3% w/w and a hull-rich fine fraction in the air stream in a zigzag classifier.
2. Pressing the kernel fraction in a screw press to a residual fat content of approx. 23% w/w at temperatures between 30 and 45° C., wherein the press cake is obtained in the form of compressed strings, hereinafter referred to as press cake pellets.
3. Deoiling of the press cake pellets with hexane in a Soxhlet apparatus to a residual fat content below 3% w/w.
4. Removing the solvent in the air stream at room temperature. The raffinate obtained in such a manner is still present in the form of the pellets and corresponds with respect to its composition to the protein flour in example 1.
5. Extracting the protein flour pellets from step 4 without further comminution by treating them with an ethanol solution using the percolation method with recirculation of the solvent until the solvent does not change anymore.
6. Repeating step 5 with fresh solvent.
7. Further treatment as in example 1, steps 7-9.
8. Use of the finished protein concentrate with or without subsequent comminution.

In this example 5, the rape kernels were present after dehulling in such a form that it was immediately possible to mechanically deoil them. A prior comminution or flaking was not carried out.

Deoiling by pressing was carried out during step 2 with a screw press. At an exit temperature of approx. 40° C., round press cake pellets with a fat content of 23% w/w (25% in DM) were obtained at the nozzle outlet of the screw press which had a high porosity and a good cohesion and a mechanical stability so that they could be used immediately for deoiling and were just strong enough to not fall apart during deoiling. At a higher pressing degree set for a residual fat content of approx. 17% w/w, these pellets were slightly denser and stronger and had a higher mechanical strength but could still be broken apart with moderate force. At a further increased pressing degree set for lower fat contents, the pellets were very strong and stable and could be broken only by means of, e.g., a mill.

Furthermore, it was found that when the pressing degree was too high, the pellets had a dark discoloration which leads to the conclusion of undesirable damages to the protein and would impair the color of the protein preparation.

It was found that at a pressing degree set for a residual fat content in the range of typically approx. 17% to 25% w/w residual fat, press cake pellets are obtained which have a good mechanical stability at a still sufficient porosity so that without further structuring or comminution during the subsequent extraction, a complete deoiling is possible.

Surprisingly, despite the loosening of the structure resulting from the removal of the oil, even after deoiling, the pellets still have a sufficient mechanical stability so that they can be subjected to an extraction with a further solvent and thus can be cleaned from non-protein substances without falling apart. Due to the porous structure, the pellets have a very favorable extraction behavior for the further extraction with alcoholic solution.

In summary, in a pressing process in which a certain residual fat content is maintained, the particles can be structured in such a manner that a subsequent structuring or comminution which usually is carried out for breaking the press cake is no longer required. Besides simplifying the method, this contributes to the conservation of the press cake so that, among other things, the protein functionality and the color in the end product can be improved.

Also, by the reduced pressing degree, the proteins are treated with care and the functional properties of the protein preparation are maintained in an improved manner. At the same time, a particle shape is produced which allows an optimal extraction and thus, the residual oil content can be further reduced after deoiling. This too, among other things, contributes to an improvement of the color of the protein preparation.

D) TABLES

TABLE 1

Composition of the rape protein preparation from the examples 1 to 3 in comparison to reference products. The listed values for the content of proteins, ash, fat and glucose are based on the dry mass (DM). The protein content was determined by determining the nitrogen by means of the Dumas method and multiplication by the factor 6.25. The ash was determined by TGA determination at 950° C. The listed fat content includes phospholipids according to Caviezel. The glucose content was determined photometrically after one extraction.

|  | DM % | Protein (N × 6.25) % (DM) | Ash % (DM) | Total fat % (DM) | Glucose % (DM) |
|---|---|---|---|---|---|
| Rape protein flour from example 1 | 91.0 | 49.0 | 8.4 | 2.8 | |
| Protein concentrate extracted with 80% isopropanol (example 1) | 91.6 | 59.5 | 9.5 | 0.7 | |
| Rape protein flour from example 2 | 90.6 | 46.8 | 8.4 | 1.7 | 7.8 |
| Protein concentrate extracted with 70% EtOH (example 2) | 83.1 | 59.3 | 8.8 | 0.5 | 1.4 |
| Rape protein flour from example 3 | 89.5 | 51.4 | 8.2 | 5.8 | |
| Protein concentrate from example 3 | 89.8 | 61.8 | 9.7 | 2.4 | |
| Soy protein isolate Supro ® Ex 33 | 94.7 | 92.2 | 3.0 | | |
| Pisane ® pea isolate | 94.9 | 89.0 | 5.1 | | |

TABLE 2

Functional properties of the rape protein preparations from the examples 1 to 3 in comparison to reference products. For analyzing the functional properties, the preparations were milled in a laboratory impact mill with sieve insert 500 μm.

|  | Protein solubility pH 7 % | Emulsifying capacity ml/g | Water binding ability ml/g (DM) | Oil binding ability ml/g |
|---|---|---|---|---|
| Rape protein flour from example 1 | 72 | 660 | | |
| Protein concentrate extracted with 80% isopropanol (example 1) | 54 | 510 | | |
| Rape protein flour from example 2 | 75 | 655 | 3.2 | 2.7 |
| Protein concentrate extracted with 70% EtOH (example 2) | 57 | 475 | 2.4 | 4.7 |

TABLE 2-continued

Functional properties of the rape protein preparations from the examples 1 to 3 in comparison to reference products. For analyzing the functional properties, the preparations were milled in a laboratory impact mill with sieve insert 500 μm.

|  | Protein solubility pH 7 % | Emulsifying capacity ml/g | Water binding ability ml/g (DM) | Oil binding ability ml/g |
|---|---|---|---|---|
| Rape protein flour from example 3 | 73 | 675 | 3.4 | 2.7 |
| Protein concentrate from example 3 | 47 | 450 | 4.8 | 2.3 |
| Soy protein isolate Supro ® Ex 33 | | 635 | | 1.5 |
| Pisane ® pea isolate | | 350 | 6.3 | 1.9 |

TABLE 3

Foam-forming functions of the rape protein preparations from the examples 1 and 3 compared to fresh hen's egg white. For analyzing the foam-forming properties, the preparations were milled in a laboratory impact mill with sieve insert 500 μm.

|  | Foam activity % | Foam stability % | Foam density g/l |
|---|---|---|---|
| Rape protein flour from example 1 | 1320 | 94 | 81 |
| Protein concentrate extracted with 80% isopropanol (example 1) | 1100 | 86 | 88 |
| Rape protein flour from example 3 | 540 | 88 | 184 |
| Protein concentrate from example 3 | 1070 | 93 | 109 |
| Hen's egg white, fresh | 1600 | 82 | 105 |

TABLE 4

Functional properties of rape protein flours (RPF) and rape protein concentrates (RPK) which are prepared with different grain sizes.

| Method | | S1 | S2 | S3 | S4 | S5 |
|---|---|---|---|---|---|---|
| RPF | untreated | >1000 | 0 | 2.5 | 3.1 | 680 |
|  | milled <500 μm | <500 | + | 3.4 | 2.7 | 675 |
| RPC | milled <500 μm | <500 | + | 4.8 | 2.3 | 450 |
|  | 2-fold milled <500 μm | <500 | ++ | 5.0 | 2.1 | |
|  | sieved: <560 μm | <560 | + | 4.7 | 2.0 | 465 |
|  | sieved <560 μm and subsequently milled <500 μm | <500 | +++ | 5.6 | | 475 |
|  | Fine material from classification (0.3-0.4) | | + | 5.3 | 2.1 | 475 |
|  | Fine material from classification (0.3-0.4), milled (500 μm) | <500 | +++ | 5.7 | | |

The columns S1-S2 have the following meaning:
S1: Grain size of the finished protein preparation in micrometer.
S2: Homogeneity, wherein "0" means a wide distribution, "+" a narrower, "++" an even narrower and "+++" a very narrow grain size distribution.
S3: Water binding ability in ml/g (DM)
S4: Oil binding ability in ml/g
S5: Emulsifying capacity in ml/g
Empty boxes in the columns S1-S2 mean that the corresponding value has not been determined.

From the preceding description, numerous modifications are at the disposal of the skilled person without departing from the scope of the invention which is defined by the claims.

Thus, e.g., it is conceivable to use the protein preparation according to the invention as basic material for producing a protein isolate which has a protein content of at least 90% in DM. The production is carried out e.g. by means of aqueous extraction of the proteins.

Further, it is conceivable to prepare the hull fractions produced during dehulling in such a manner that they can be utilized energetically so as to generate electricity and/or usable heat. Preparing the hull fractions can take place, among other things, in such a manner that the hulls are deoiled e.g. by pressing and/or by means of solvent, and/or are pelletized. Energy recovery can be carried out, e.g. by burning.

If necessary, wood and/or a different kind of suitable biomass is added to the hulls so as to improve the burning. Said biomass can also originate from the preparation of the rape seeds before they are being dehulled and can be, e.g., in the form of impurities during raw material supply (debris, contaminants, etc.) and/or in the form of undersized and oversized grains (portion of the rape seeds which is removed prior to dehulling so as to obtain rape seeds for dehulling with a size as uniform as possible).

Preferably, rape components originating from kernels produced during dehulling the rape seeds or from fractions obtained from these kernels are not or only to a limited extent added to the hulls to be burnt so that the ratio of the mass of rape components to the mass of hulls is smaller than 1 to 1, preferred smaller than 1 to 2 and particularly preferred smaller than 1 to 5.

E) GLOSSARY mg: milligram
ml: milliliter
RPC: rape protein concentrate
RPF: rape protein flour
DM: dry mass
Percent v/v ("volume per volume"): percent by volume, determined at a temperature of 25 degrees Celsius (volume fraction of a component with respect to the volume of a mixture)
Percent w/w ("weight per weight"):
Percent by mass/percent by weight

The invention claimed is:

1. A protein preparation produced from rapeseeds,
the protein preparation being produced by a method wherein the rapeseeds are dehulled so as to obtain a kernel fraction having a hull content of less than 5% w/w, and
the kernel fraction is then further processed such that the protein preparation is free of sulfur dioxide,
wherein the protein preparation has:
a protein content of less than 90% based on the dry mass,
a brightness $L^*$, determined according to a CIE-$L^*a^*b^*$ color scale, of at least 80, and
at least water-binding, oil-binding and emulsifying functionality, wherein
the water binding ability is at least 1 ml per gram of dry mass, and/or
the oil binding ability is at least 1 ml/g, and/or
the emulsifying capacity is at least 400 ml/g, and
the protein preparation is free of sulfur dioxide.

2. The protein preparation according to claim 1, wherein the values for $a^*$ and $b^*$ according to the CIE-$L^*a^*b^*$ color scale lie in the range of $-5<a^*<+5$, and $-5<b^*<+30$.

3. The protein preparation according to claim 1, wherein
the water binding ability of the protein preparation is at least 3 ml per gram of dry mass, and/or
the oil binding ability is at least 2 ml/g, and/or
the emulsifying capacity is at least 600 ml/g.

4. The protein preparation according to claim 1, wherein the protein preparation has a protein solubility greater than 40%.

5. The protein preparation according to claim 1, wherein the protein preparation is free of mustard-like and/or horseradish-like odor and/or taste, and/or causes no astringency in case of oral intake.

6. The protein preparation according to claim 1, wherein the protein preparation additionally has foam-forming functionality.

7. The protein preparation according to claim 6, wherein the protein preparation has at least one of the following foam-forming properties:
the foam activity corresponds to at least 30% of the foam activity of hen's egg white,
the foam density corresponds to 50% to 200% of the foam density of whipped egg whites,
the foam stability corresponds to at least 80% of the foam stability of whipped egg white.

8. The protein preparation according to claim 1, wherein the protein content based on the dry mass is in a range of 40% to 80%.

9. The protein preparation according to claim 1, wherein the protein preparation has a crude fiber content, based on the dry mass, in a range of 3% to 30%.

10. The protein preparation according to claim 1, wherein the protein preparation has a fat content, based on the dry mass, that is less than 6%.

11. The protein preparation according to claim 1, wherein the protein preparation has at least one content selected from the group consisting of:
phytic acid content, based on the dry mass, of less than 10%,
glucosinolates content of less than 4000 mg per kg of protein preparation,
progoitrin content of less than 1000 mg per kg of protein preparation, and
phenolic acid content, based on the dry mass, of less than 5%.

12. A product in the form of a rape protein flour, a rape protein concentrate, a protein isolate having a protein content of at least 90% based on the dry mass, a foodstuff, a feedstuff, a fish food, an ingredient for foodstuff, a product for technical applications or a cosmetic product, produced with a protein preparation according to claim 1.

13. The protein preparation according to claim 1, wherein the brightness $L^*$ is at least 90, and/or the values for $a^*$ and $b^*$ are in the range of $-1<a^*<+3$, and $0<b^*<+20$.

14. The protein preparation according to claim 1, wherein the protein preparation has a protein solubility greater than 60%.

15. The protein preparation according to claim 5, wherein the protein preparation is odorless and/or tasteless.

16. The protein preparation according to claim 7, wherein the protein preparation has the following foam-forming properties:
foam activity corresponding to at least 50% of the foam activity of hen's egg white, and
foam stability corresponding to at least 100% of the foam stability of whipped egg white.

17. The protein preparation according to claim 1, wherein the protein content is in a range of 45% to 65% based on the dry mass.

18. The protein preparation according to claim 1, wherein the protein preparation has a crude fiber content, based on the dry mass, in a range of 5% to 10%.

19. The protein preparation according to claim 1, wherein the protein preparation has a fat content, based on the dry mass, that is less than 3%.

20. The protein preparation according to claim 11, wherein the protein preparation has
   phytic acid content, based on the dry mass, of less than 3%,
   glucosinolates content of less than 1500 mg per kg of protein preparation,
   progoitrin content of less than 200 mg per kg of protein preparation, and
   phenolic acid content, based on the dry mass, of less than 0.5%.

21. The protein preparation according to claim 1, being in the form of a pourable material containing grains with a size of less than 1 mm, the protein preparation having a water binding ability of at least 3 ml per gram of dry mass.

* * * * *